United States Patent
Frechin et al.

(10) Patent No.: US 7,392,138 B2
(45) Date of Patent: Jun. 24, 2008

(54) METHOD FOR DETERMINING THE CONTENT OF AT LEAST ONE GIVEN GAS IN A DRILLING MUD, ASSOCIATED DEVICE AND RIG

(75) Inventors: Nicolas Frechin, Paris (FR); Jérôme Breviere, Taverny (FR)

(73) Assignee: Geoservices, Le Blanc-Mesnil (FR)

( * ) Notice: Subject to any disclaimer, the term of this patent is extended or adjusted under 35 U.S.C. 154(b) by 19 days.

(21) Appl. No.: 11/395,264

(22) Filed: Apr. 3, 2006

(65) Prior Publication Data

US 2006/0224333 A1    Oct. 5, 2006

(30) Foreign Application Priority Data

Apr. 4, 2005    (FR) .................................. 05 03317

(51) Int. Cl.
    *G06F 19/00*    (2006.01)

(52) U.S. Cl. .................... 702/9; 702/6; 702/24; 702/25; 73/863.12; 422/68.1; 422/83

(58) Field of Classification Search .................... 702/9, 702/24, 25, 6; 73/200, 863.12, 23.36, 23.41, 73/23.42, 152.04, 152.19, 152.42; 422/68.1, 422/83

See application file for complete search history.

(56) References Cited

U.S. PATENT DOCUMENTS

| | | | | |
|---|---|---|---|---|
| 4,635,735 A | * | 1/1987 | Crownover | ................... 175/48 |
| 4,887,464 A | * | 12/1989 | Tannenbaum et al. | ..... 73/152.04 |
| 5,049,738 A | | 9/1991 | Gergely et al. | |
| 5,375,465 A | | 12/1994 | Carlson | |
| 5,859,430 A | | 1/1999 | Mullins et al. | |

* cited by examiner

*Primary Examiner*—John E Barlow, Jr.
*Assistant Examiner*—Hien X Vo
(74) *Attorney, Agent, or Firm*—Wenderoth, Lind & Ponack, L.L.P.

(57) ABSTRACT

A method includes the phases of measuring the quantity of a given gas in the gases extracted from a calibration sample of a calibration mud, in at least two stages for extraction under predetermined conditions. A family of curves representing the extraction, under the predetermined conditions, of the given gas from the drilling mud, is established on the basis of the measurements carried out. The method also includes the phases of measuring the quantity of given gas in the gases extracted from an analysis sample of the drilling mud in an extraction stage, under the predetermined conditions; and computing the given gas content of the drilling mud on the basis of the measured quantity of given gas and of a curve of the family.

19 Claims, 6 Drawing Sheets

METHOD FOR DETERMINING THE CONTENT OF AT LEAST ONE GIVEN GAS IN A DRILLING MUD, ASSOCIATED DEVICE AND RIG

TECHNICAL FIELD

The present invention relates to a method for determining the content of at least one given gas in a drilling mud.

BACKGROUND TO THE INVENTION

During the drilling of a well containing oil or another effluent (in particular gas, steam, water), it is known to analyze the gaseous compounds contained in the drilling muds emerging from the well. This analysis facilitates the reconstruction of the geological sequence of the formations passed through during the drilling process and helps to determine possible uses for the fluid deposits encountered.

This analysis, which is carried out continuously, includes two main phases. The first phase consists in extracting the gases conveyed by the mud (for example, hydrocarbon compounds, carbon dioxide and hydrogen sulphide). The second phase consists in qualifying and quantifying the extracted gases.

A degasser having a mechanical stirring means of the type described in FR 2 799 790 is frequently used for extracting the gases from the mud. The gases extracted from the mud, which are mixed with a carrier gas introduced into the degasser, are conveyed by suction through a gas extraction conduit up to an analyzer, which allows the extracted gases to be quantified.

A method of this type is not entirely satisfactory, especially for oil or synthetic product-based muds. The kinetics for the extraction of the gases from the degasser is, in particular, dependent on the solubility of the gases in the mud. For example, for an oil drilling mud, $C_4$ hydrocarbon gases are extracted more slowly than $C_1$ hydrocarbon gases.

Given the limited residence time of the mud in the degasser, determining the relative or absolute content of the gases contained in the drilling mud from quantities of gases extracted from the degasser requires complex mathematical models and is imprecise.

The main object of the invention is therefore to determine, in a precise yet simple manner, the content of at least one given gas contained in a drilling mud, during a drilling process.

SUMMARY OF THE INVENTION

The invention accordingly relates to a method for determining the content of at least one given gas in a drilling mud, and comprises a calibration step including the following phases.

(i) Measuring an item of data representing the quantity of given gas in the gases extracted from a calibration sample of a calibration mud. The measurement is done in at least two stage for the extraction, under predetermined conditions, of the calibration sample gases.

(ii) Establishing a family of curves representing the extraction, under the predetermined conditions, of the given gas contained in the drilling mud, on the basis of the measurements carried out during the stages for the extraction of the calibration sample gases. At least one analysis step including the following phases.

(a) Measuring an item of data representing the quantity of given gas in the gases extracted from an analysis sample of the drilling mud in a stage for the extraction, under the predetermined conditions, of the analysis sample gases.

(b) Computing the given gas content of the drilling mud, on the basis of the quantity of given gas measured in step (a) and of a curve of the gas family.

The method according to the invention may comprise one or more of the following characteristics, in isolation or in any technically possible combination.

During step (i), each extraction stage can include the steps of introducing, at a given temperature, the calibration sample into a first gas extraction vessel provided with a stirring means. The gases extracted from the vessel are sampled. During step (a), the extraction stage includes the steps of introducing, substantially at the given temperature, the analysis sample into a second vessel similar to the first vessel, and sampling the gases extracted from the second vessel.

During step (i), each extraction stage can include a step for recovering the calibration sample after the step of sampling the extracted gases.

During step (i), the number of extraction stages can be between 2 and 6.

The family of curves can comprise at least one exponential function, and can comprise sequences having the general formula:

$$q_n = q_1 \exp[-b(n-1)] \tag{1}$$

wherein n is the nth extraction stage of the extraction phase; $q_n$ is the quantity of given gas in the gases extracted during the nth extraction stage; $q_1$ is the quantity of given gas in the gases extracted during the first extraction stage; and (b) is a parameter that is independent of the given gas content of the calibration mud and that is dependent on the characteristics of the mud and the predetermined conditions.

Phase (b) can include the steps of identifying the curve of the family on which is located a point corresponding to the quantity of given gas measured in step (a) and in the stage for the extraction of the analysis samples. This quantity of given gas measured in step (a) is added to at least one quantity of given gas corresponding to a different point on the curve.

The drilling mud can be an oil-based mud or a mud based on at least one synthetic compound.

The calibration mud can comprise at least one portion of the drilling mud.

The invention also relates to a device for determining the content of at least one given gas in a drilling mud, of the type comprising calibration means comprising a first means for the extraction, under predetermined conditions, of the gas contained in a calibration sample of a calibration mud; and a first means for measuring an item of data representing the quantity of at least one given gas in the gases extracted from the calibration sample, in at least two stages for extraction, under the predetermined conditions, in the first extraction means. A means is provided for establishing a family of curves representing the extraction, under the predetermined conditions, of the given gas contained in the drilling mud, on the basis of the measurements carried out by the first measuring means. An analysis means comprises a second means for the extraction, under the predetermined conditions, of the gas contained in an analysis sample of the drilling mud; and a second means for measuring an item of data representing the quantity of given gas in the gases extracted from the analysis sample, in a stage for extraction, under the predetermined conditions, in the second extraction means. In addition, a means is provided for computing the given gas content of the drilling mud, on the basis of the quantity of given gas measured by the second measuring means and of a curve of the family.

The device according to the invention may comprise one or more of the following characteristics, in isolation or in any technically possible combination.

The first and second extraction means can each comprise at least one vessel provided with a stirring means. Each vessel can also comprise a means for conveying mud into the vessel; a means for evacuating mud outside the vessel; and a means for sampling the gas extracted from the vessel, and the vessels having similar structures.

The first extraction means can comprise a single vessel and means for recovering mud at the outlet of the evacuation means, which means may be connected to an inlet of the vessel.

The first extraction means can consist of the second extraction means.

The first extraction means can comprise at least two vessels having similar structures, the means for evacuating mud from the first vessel being connected to the means for conveying mud to the second vessel.

The invention also relates to a drilling rig of the type comprising a conduit for the circulation of a drilling mud. The drilling rig comprises a device as defined above; and a means for sampling mud from the circulation conduit.

BRIEF DESCRIPTION OF DRAWINGS

Embodiments of the invention will now be described with reference to the accompanying drawings, in which.

DETAILED DESCRIPTION OF PREFERRED EMBODIMENTS

A device according to the invention is used, for example, in a drilling rig of an oil production well.

Figure 1:
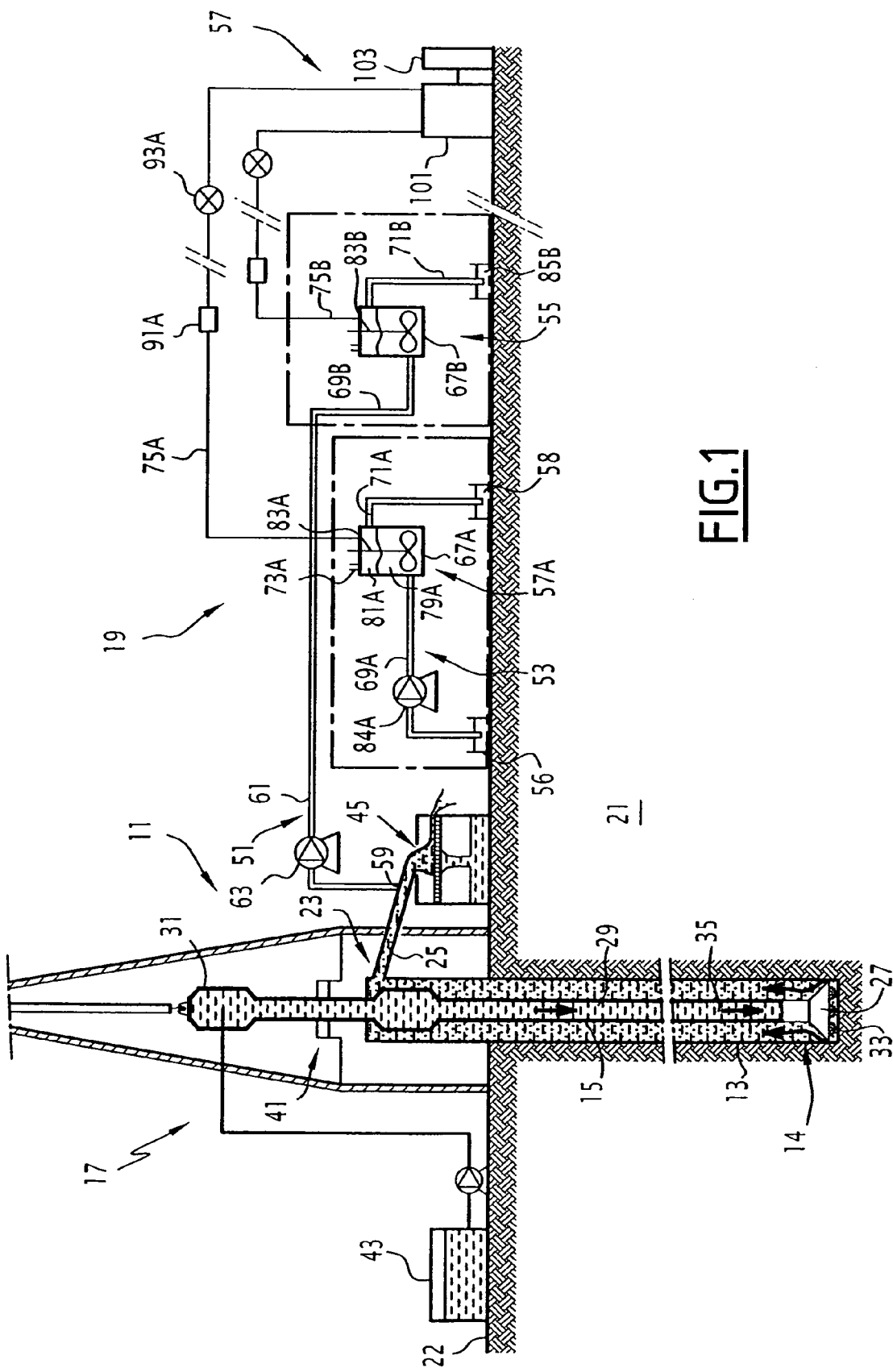
FIG. 1 is a schematic vertical section of a drilling rig provided with a first device according to the invention.

As illustrated in FIG. 1, this rig 11 comprises a drilling conduit 13 in a cavity 14 formed by a rotational drilling tool 15, a surface rig 17 and an analyzing device 19 according to the invention.

The drilling conduit 13 is disposed in the cavity 14 formed in the subsoil 21 by the rotational drilling tool 15. This conduit 13 comprises, at the surface 22, a wellhead 23 provided with a drain 25.

The drilling tool 15 comprises a drilling head 27, a drill string 29 and a liquid-injection head 31.

The drilling head 27 comprises a penetrating member 33 for penetrating the rocks of the subsoil 21. It is mounted on the lower portion of the drill string 29 and is positioned at the bottom of the drilling conduit 13.

The string 29 comprises a set of hollow drill pipes. These pipes delimit an internal space 35, which allows a liquid to be conveyed from the surface 22 up to the drilling head 27. The liquid-injection head 31 is accordingly screwed to the upper portion of the string 29.

The surface rig 17 comprises driving member 41 for supporting and driving the drilling tool 15 in rotation, an injection member 43 for injecting the drilling liquid, and a vibrating screen 45.

The injection member 43 is hydraulically connected to the injection head 31 for introducing a liquid and causing it to circulate within the internal space 35 of the drill string 29.

The vibrating screen 45 collects the liquid filled with drilling residues (referred to hereinafter as "drilling mud") issuing from the drain 25 and separates the liquid from the solid drilling residues.

As illustrated in FIG. 1, the device 19 according to the invention comprises a calibration stage 53 and an analysis stage 55. The device also comprises analysis and computation means 57, which are common to the calibration stage 53 and to the analysis stage 55.

The calibration device 53 comprises a tank 56 for receiving a sample of calibration mud, a gas extraction device 57A, and a tank 58 for holding mud evacuated from the extraction means.

The gas extraction member 57A is of the type described in patent application FR 2 799 790. This member 57A comprises a vessel 67A, a conduit 69A for conveying mud into the vessel 67A, a conduit 71A for evacuating mud from the vessel 67A, a port 73A for introducing a carrier gas into the vessel 67A, and a conduit 75A for extracting the gases extracted from the vessel 67A.

The vessel 67A comprises a lower portion 79A, in which the mud circulates, and an upper portion 81A, which has a gas ceiling. This vessel 67A is also provided with a mechanical stirrer 83A.

The mud-conveying conduit 69A extends between the tank 56 and the vessel 67A. This conveying conduit 69A is provided with a sampling pump 84A and advantageously with means (not shown) for heating the mud, to bring the temperature of this mud to between 25 and 120° C., preferably between 60 and 90° C.

The mud-evacuation conduit 71A extends between an overflow passage, formed in the upper portion 81A of the vessel 67A, and the holding tank 58.

The port 73A for introducing a carrier gas into the vessel 67A comprises a vent for introducing air under atmospheric pressure into the vessel 67A.

The extraction conduit 75A extends between an extraction opening, formed in the upper portion 81A of the vessel 67A, and the analysis and computation device 57.

The extraction conduit 75A comprises a flow regulator 91A and a vacuum pump 93A, which allows the gases extracted from the vessel to be conveyed by suction up to the analysis and computation device 57.

The analysis stage 55 comprises a mud-sampling member 51, a second gas-extraction member 57B and a mud-holding tank 85B.

The sampling member 51 comprises a liquid-sampling head 59, mounted so as to protrude from the drain 25, and a connecting pipe 61.

The connecting pipe 61 is provided with a sampling pump 63, for example a peristaltic pump, and extends between the head 59 and the vessel 67B of the sampling member.

The gas extraction member 57B for extracting gases from the analysis stage 55 is identical in terms of its structure to the member 57A for extraction from the calibration stage.

The vessels 67A and 67B of the calibration and analysis stages 53 and 55 are thus identical in terms of structure, in particular in terms of their geometry and in terms of the nature of the stirrer 83A and 83B.

Moreover, the conduit 75B for extracting gas from the analysis stage 55 is connected to the analysis device 57.

The conduit 71B for evacuating mud from the stage 55 is connected directly to a holding tank 85B.

The analysis and computation means 57 comprise a control means 101 and a computer 103.

A controller 101 is provided with a selective gas collector, which selectively receives the gases extracted by one or the other of the respective conduits 75A or 75B for extraction from the calibration stage 53 and the analysis stage 55, and which conveys these extracted gases up to at least one measuring device.

The measuring device is, for example, an infrared detection device for carbon dioxide quantification, an FID (flame-ionization detector) chromatograph for detecting hydrocarbons, or a TCD (thermal conductivity detector), depending on the gases to be analyzed. It is thus possible simultaneously to detect and to quantify a plurality of gases, in particular if the controller 101 comprises a plurality of measuring devices.

In the illustrated example, at least one device generates an electrical signal, as a function of the quantity of given gas in the collected extracted gases, and transmits this signal to the computer 103.

The method according to the invention for determining the content of at least one given gas during a well-drilling phase will now be described by way of example and with reference to FIG. 1 and to the flow charts of FIGS. 2 and 3.

The given gases analyzed using this method are, for example, $C_1$ to $C_6$ hydrocarbons, preferably $C_1$ to $C_5$ hydrocarbons.

During the drilling phase, the drilling tool 15 is driven in rotation by the surface rig 41. A drilling liquid is introduced by the injection member 43 into the internal space 35 of the drill string 29. This liquid goes down to the drilling head 27 and enters the drilling conduit 13 through the drilling head 27. This liquid cools and lubricates the penetrating member 33. The liquid then collects the waste material resulting from the drilling process and rises via the annular space defined between the drill string 29 and the walls of the drilling conduit 13. The drilling mud thus formed (i.e., the mud to be examined, or the "examination sample") is evacuated via the drain 25.

The term "drilling phase" refers, in this case, to the process of introducing the drilling conduit 13 into a substantially homogeneous subsoil formation. The composition of the drilling liquid introduced into the space 35 during a drilling phase is substantially constant.

The drilling mud evacuated via the conduit 25 is, for example, a water-based mud, an oil-based mud or a synthetic material-based mud, depending on the nature of the drilling liquid introduced into the rig 11.

Figure 2:
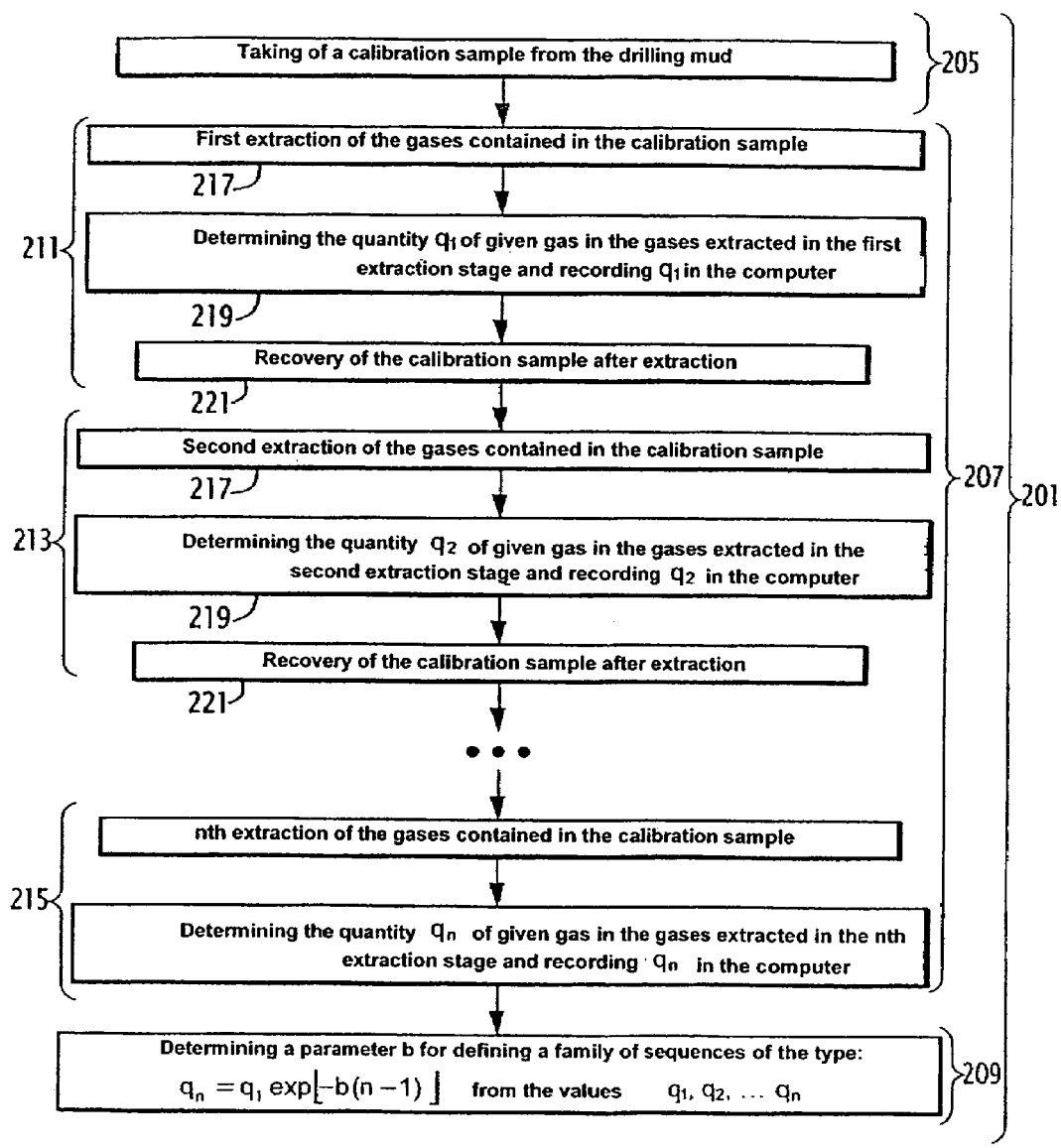
FIG. 2 is a flow chart specifying a calibration step in a method according to the invention.
Figure 3:
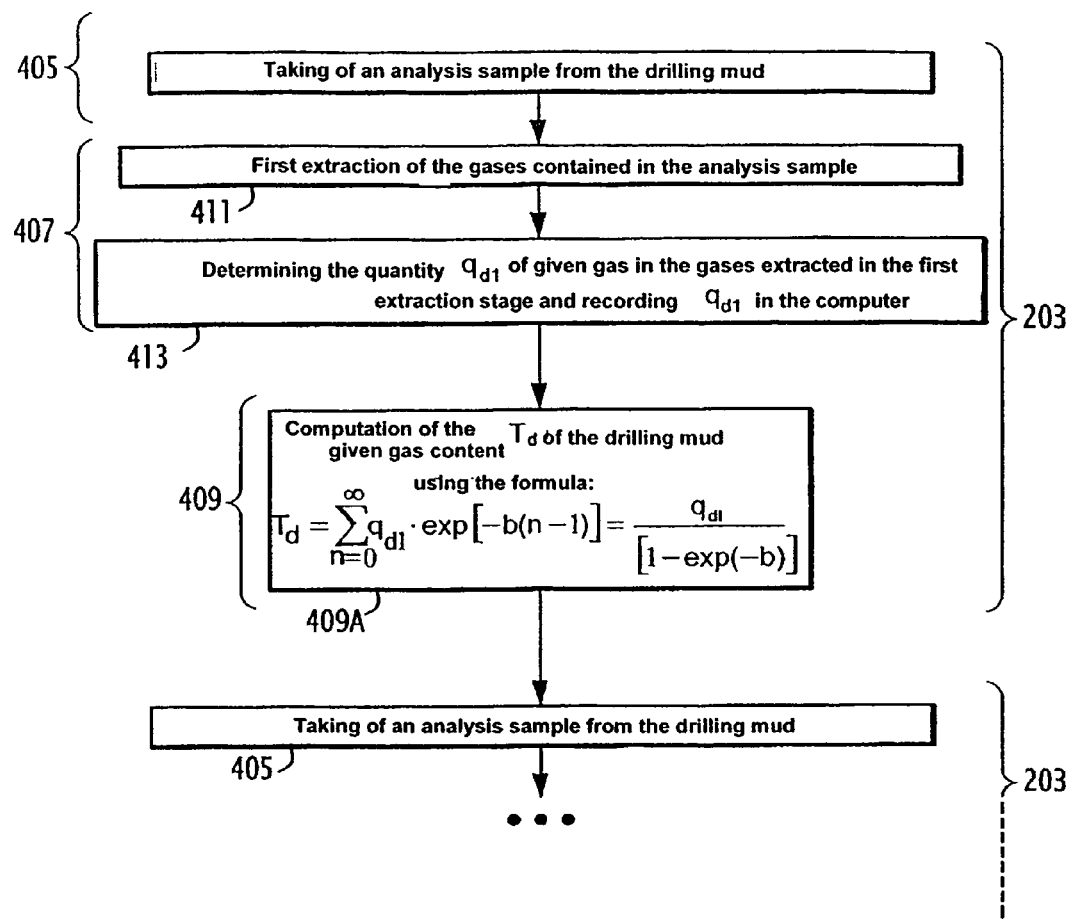
FIG. 3 is a flow chart specifying an analysis step in a method according to the invention.

As illustrated in FIGS. 2 and 3, the method according to the invention includes, for each drilling phase, at least one calibration step 201 and a plurality of analysis steps 203.

The number of calibration steps 201 is less than the number of analysis steps 203. Preferably, a single calibration step 201 is carried out for all of the analysis steps 203 during a single drilling phase.

As illustrated in FIG. 2, the calibration step 201 includes, in succession, a sampling phase 205, a measuring phase 207 and a computation phase 209.

In the sampling phase 205, a calibration sample of the drilling mud (examination sampled) circulating in the drain 25 is collected in the receiving tank 56. This sample has a predetermined volume that is, for example, greater than 150 times the volume of the vessel 67A. Preferably, this volume is approximately 200 times the volume of the vessel 67A.

The pump 84A of the calibration stage 53 is activated in such a way that the calibration sample is conveyed up to the vessel 67A of the calibration stage 53 through the mud-conveying conduit 69A.

The measuring phase 207 includes at least two consecutive extraction stages 211, 213, 215 carried out on a single calibration sample.

In a first extraction stage 211, the calibration sample containing an initial given gas content $T_0$, is introduced into the vessel 67A, for example at a rate of 0.3 liters per minute. In the vessel 67A, a first portion of the gases contained in the calibration sample is extracted from this sample and collected, in step 217, in the upper portion 81A under predetermined conditions—in particular, temperature, residence time and stirring speed conditions. In the example illustrated in FIG. 1, the temperature of the sample is substantially equal to 90° C. and the residence time in the vessel is approximately 16 seconds.

The first portion $q_1$ of the given gas initially contained in the calibration sample is therefore extracted from this sample into the gas ceiling of the vessel 67A.

The extracted gases are sampled by suction via the extraction conduit 75A and conveyed up to the controller 101 through this conduit 75A, via the flowmeter 91A and the vacuum pump 93A. The suction rate is, for example, substantially equal to 500 cm$^3$/min.

The controller 101 then qualifies the gases extracted from the vessel and generates a signal representing the quantity $q_1$ of given gas in these extracted gases. This quantity $q_1$ is then recorded, in step 219, in the computer 103 and is associated by the computer 103 with an integer corresponding to the current extraction stage (point 301 in FIG. 4).

Substantially the entire calibration sample is then recovered in the holding tank 58.

The holding tank 58 and the receiving tank 56 are then swapped over. The tank 58, containing all of the calibration sample recovered after its passage into the vessel 67A, is thus connected to the sampling conduit 69A.

Once it has undergone the first extraction stage, the same calibration sample is therefore recovered in step 221 and reintroduced in its entirety into the vessel 67A, where it undergoes a second extraction stage 213.

The given gas content $T_1$ contained in the calibration sample prior to the second extraction stage is substantially equal to the difference between the initial given gas content $T_0$ of the mud and the quantity of gas $q_1$ extracted from the mud during the first extraction stage.

The calibration sample then undergoes a second extraction stage 213, which includes the same steps 217, 219, 221 as the first extraction stage 211.

A second portion $q_2$ of given gas is extracted from the mud during the second extraction stage 213.

At least two extraction stages 211, 213, 215 are required for carrying out the method according to the invention. In the illustrated example, the number of extraction stages is between 2 and 6.

Figure 4:
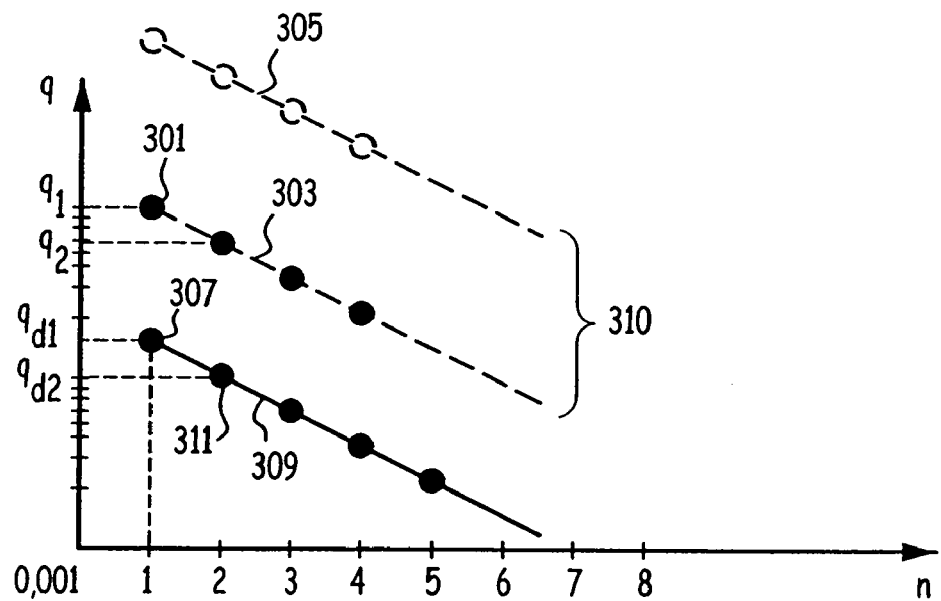
FIG. 4 is a graph showing a family of curves representing the extraction of a given gas from a device according to the invention.

In the computation phase 209, the computer 103 determines the definition of a sequence represented, in logarithmic scale, by the curve 303 of FIG. 4, from at least two pairs of values (n, $q_n$) corresponding to two stages n for the extraction of the gases from the calibration sample and to the quantity of given gas $q_n$ in the gases extracted during the extraction stages n. This sequence depends on the quantity $q_1$ of given gas extracted during a first extraction stage 211 and on a parameter b, which is characteristic of the mud.

As illustrated in FIG. 4, the sequence represented by the curve 303 is substantially an exponential geometric sequence, which is advantageously described by the formula $$q_n = q_1 \exp[-b(n-1)] \quad (1)$$

wherein n is the nth extraction stage; $q_1$ is the quantity of given gas in the gases extracted during the first extraction stage; $q_n$ is the quantity of given gas in the gases extracted during the nth extraction stage; and b is a parameter that is independent of the initial given gas content $T_0$ of the calibration sample.

The parameter b thus depends solely on the characteristics of the mud, in particular its composition, and on the predetermined conditions.

Therefore, if the calibration step 201 was carried out using a calibration sample initially comprising a different given gas content $T_{d0}$, the measuring phase 207 carried out using this sample would allow, during the computation phase 209, a sequence represented by a curve 305 parallel to the first curve 303 to be obtained, in logarithmic scale.

Determining the parameter b therefore establishes a family 310 of sequences (calibration curves) represented by the curves 303, 305, 309, respectively, and representing the extraction, under the predetermined conditions, of the given gas contained in the drilling mud. These curves are described by general formula (1) in which, for the example illustrated in FIG. 1, n and $q_1$ are the parameters defining the family.

As illustrated in FIG. 3, each analysis step includes a sampling phase 405, a measuring phase 407 and a computation phase 409.

In the sampling phase 405, the sampling pump 63 of the analysis stage 55 is activated in order to take an analysis sample of the drilling mud (examination sample) from the drain 25.

The analysis sample is conveyed up to the vessel 67B via the conveying conduit 69B of the analysis stage.

The measuring step 407 includes a single extraction stage 411.

In the extraction stage, the analysis sample initially contains a given gas content $T_d$ to be determined. This sample is introduced into the vessel 67B of the analysis stage 55, in which the predetermined conditions used in the vessel 67A of the calibration stage 53 during the calibration step (in particular, temperature, residence time and stirring speed) are reproduced.

The gases extracted from the analysis sample are sampled via the extraction conduit 75B and are conveyed up to the analysis and computation device 57.

A signal representing the quantity $q_{d1}$ of given gas in the gases extracted from the analysis sample during this single extraction stage is then generated by the controller 101, and the quantity $q_{d1}$ is recorded by the computer 103 (step 413) and associated with the first extraction stage (point 307 in FIG. 4).

In the computation phase 409A, the computer 103 identifies the curve 309 of the family 310 of sequences on which is located the point 307 corresponding to the quantity $q_{d1}$ of given gas in the gases extracted from the analysis sample and to the extraction stage in which the quantity $q_{d1}$ of given gas was collected. In the illustrated example, this curve 309 passes via the intersection 307 between a line parallel to the x-axis, passing via the values $q_{d1}$ of the y-axis, and a line parallel to the y-axis, passing via the point 1 of the x-axis, which corresponds to the first extraction stage in the vessel 67.

The computer 103 then computes the initial given gas content $T_{d0}$ of the analysis sample by adding the quantity $q_{d1}$ of given gas in the gases extracted from the analysis sample to the quantity $q_{d2}$ of given gas corresponding to at least one other point 311 on the identified curve.

In the computation step 409A, the content $T_d$ is computed using the formula:

$$T_d = \sum_{n=1}^{\infty} q_{d1} \cdot \exp[-b(n-1)] = \frac{q_{d1}}{[1-\exp(-b)]}, \quad (2)$$

wherein $q_{d1}$ is the quantity of given gas in the gases extracted from the analysis sample and b is the parameter determined in the calibration step.

In a variation (not shown), the initial given gas content is computed using the formula:

$$T_d = \sum_{n=1}^{N} q_{d1} \exp[-b(n-1)], \quad (3)$$

wherein N is an integer representing the number of points used for carrying out the addition, $q_{d1}$ is the quantity of given gas in the gases extracted from the analysis sample, and b is the parameter determined in the calibration step.

In practice, N is greater than or equal to 2, and preferably between 4 and 6.

The number N is determined as a function of the capacity of the given gas to be extracted from the drilling mud in the vessel 67B, under the predetermined conditions.

Figure 5:
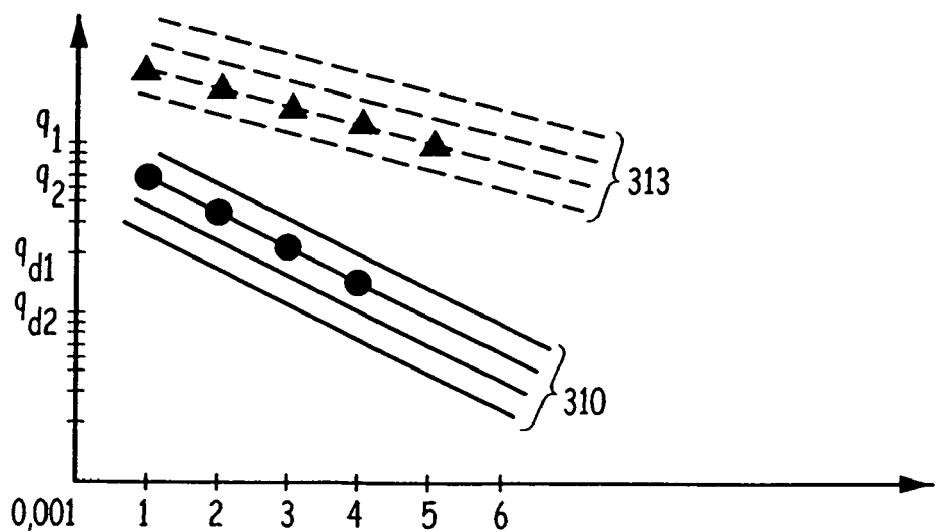
FIG. 5 is a view similar to FIG. 4 for two separate given gases.

As illustrated in FIG. 5, a separate family 313, 310 of calibration curves is thus obtained for each given gas. In FIG. 5, the first given gas, corresponding to the family 313 illustrated at the top of the figure, has less rapid extraction kinetics than the second given gas, corresponding to the family 310 at the bottom of the figure. A greater number of points $N_1$ is therefore selected in formula (3) for computing the first given gas content than the number of points $N_2$ selected for computing the second given gas content.

Moreover, if at least two given gases are quantified simultaneously by the controller 101, the relative content of each of the given gases in the drilling mud is determined relative to the overall gas content of the mud.

In a variation, a correction factor is applied for quantitatively determining the content of a given gas in the drilling mud.

Figure 6:
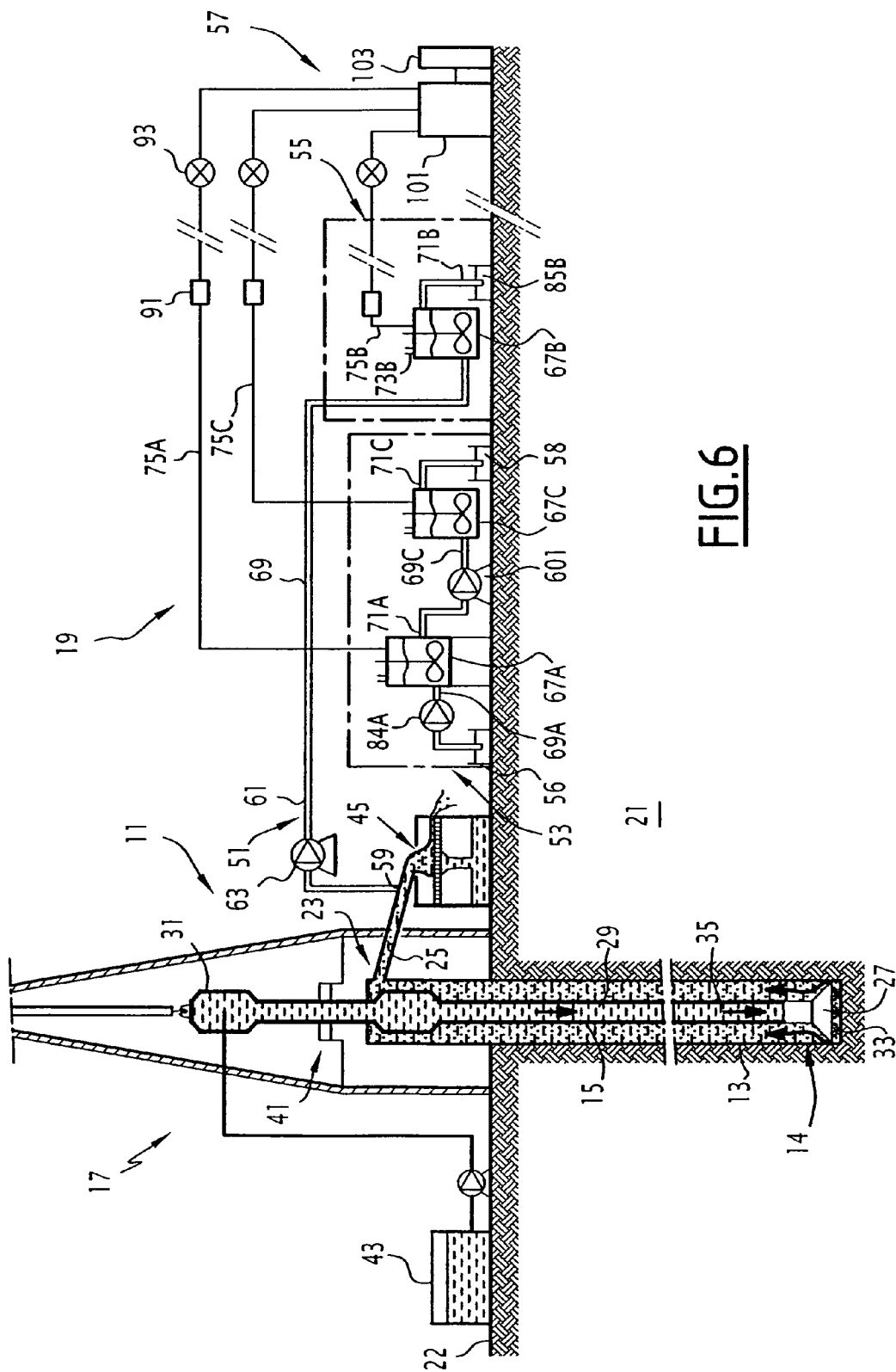
FIG. 6 is a view similar to FIG. 1, the rig being provided with a second device according to the invention.

In a second device according to the invention, illustrated with regard to FIG. 6, the calibration stage 53 comprises two vessels 67A and 67C, which have identical structures and are mounted in series. The conduit 71A for evacuating mud from the first vessel 67A is thus connected to the conduit 69C for conveying mud to the second vessel 67C via a pump 601. The conduit 71C for extracting mud from the second vessel 67C is connected to the holding tank 58.

During the calibration stage 201, the first extraction stage 211 is carried out in the first vessel 67A as described above.

The calibration sample is then recovered and conveyed up to the second vessel 67C, where it undergoes the second extraction stage 213.

In a variation of this second device, the calibration stage 53 may comprise a plurality of vessels 67, mounted in series.

Figure 7:
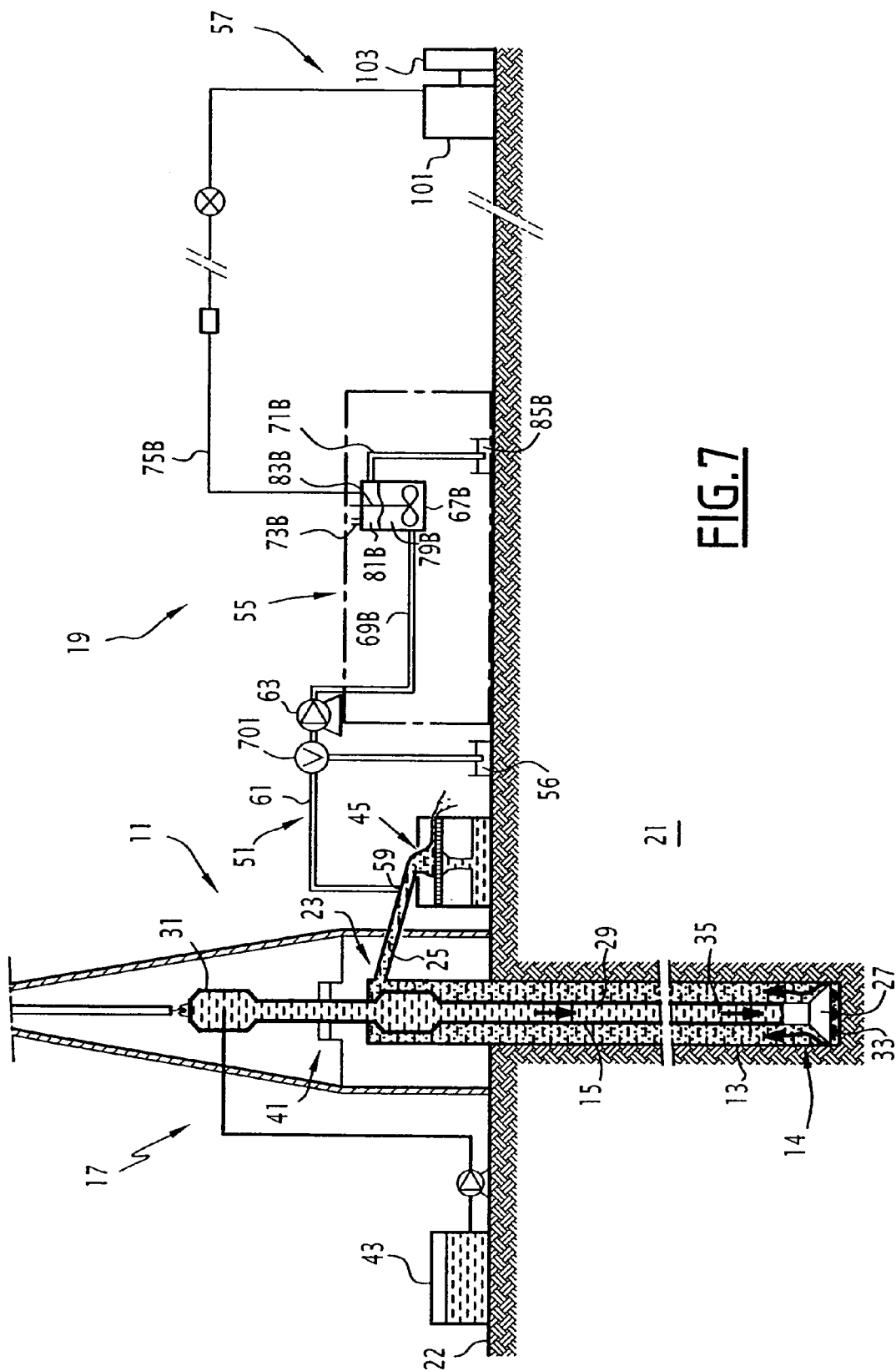
FIG. 7 is a view similar to FIG. 1, the rig being provided with a third device according to the invention.

In a third device according to the invention, illustrated with regard to FIG. 7, the calibration stage 53 consists of the analysis stage 55.

A three-way valve 701 is interposed on the connecting pipe 61 upstream of the sampling pump 63. The valve 701 comprises an inlet connected to the receiving tank 56 and an inlet connected to the sampling head 59. It comprises an outlet connected to the inlet of the pump 63 on the mud-conveying conduit 69B.

The three-way valve 701 is controlled for selectively sending to the vessel 67B the mud collected by the sampling means 51 during the analysis step, or the mud contained in the receiving tank 56 during the calibration step. The operation of this device is also similar to that of the first device.

In this device, the calibration step 201 is carried out, for example, at the end of a drilling phase. During the drilling phase, analysis samples are continuously taken and each undergo a measuring phase 407. The computation phase 409A corresponding to each analysis sample is then carried out at the end of the drilling phase, after the calibration step 201.

In a variation, the calibration sample is obtained from a calibration mud separate from the drilling mud (examination sample).

In another variation, the family of curves 213 comprises a polynomial sequence or another mathematical function.

The above-described invention provides a method for determining, using simple means, the content of at least one given gas in a drilling mud. This method does not require the use of complex physico-chemical models, in particular for oil muds or muds of synthetic origin.

The invention claimed is:

1. A method of determining a content of a given gas in a drilling mud, comprising:
   initially extracting and collecting a first portion of the given gas from a calibration sample of the drilling mud under predetermined conditions;
   subsequently extracting and collecting a second portion of the given gas from the same calibration sample of the drilling mud under the predetermined conditions;
   measuring the extracted first portion and the extracted second portion of the given gas to obtain data representing a quantity of the first portion of the given gas and a quantity of the second portion of the given gas extracted from the calibration sample of drilling mud;
   establishing a family of calibration curves representing the given gas extracted from the calibration sample of the drilling mud, said establishing of the family of calibration curves being based on the data obtained during said measuring of the extracted first portion and the extracted second portion of the given gas;
   measuring the given gas extracted from an analysis sample of the drilling mud to obtain data representing a quantity of the given gas extracted from the analysis sample of the drilling mud, the given gas being extracted from the analysis sample under the predetermined conditions; and
   computing a content of the given gas in the drilling mud based on the data representing the quantity of the given gas extracted from the analysis sample and based on an applicable curve of the established family of calibration curves.

2. The method of claim 1, wherein each of said initially extracting and collecting the first portion and said subsequently extracting and collecting the second portion includes:
   introducing the calibration sample at a given temperature into a first gas extraction vessel having stirring member; and
   sampling the gases extracted from the vessel; and
   wherein said measuring of the portion of the given gas extracted from the analysis sample of the drilling mud includes:
   introducing the analysis sample substantially at the given temperature into a second vessel; and
   sampling the gases extracted in the second vessel.

3. The method of claim 2, wherein each of said initially extracting and collecting the first portion and said subsequently extracting and collecting the second portion includes recovering the calibration sample after extracting the gas.

4. The method of claim 1, wherein said initially extracting and collecting the first portion comprises a first extraction stage, and said subsequently extracting and collecting the second portion comprises a second extraction stage, wherein said method includes no more than a total of six extraction stages.

5. The method of claim 1, wherein the established family of calibration curves comprises at least one exponential function.

6. The method of claim 5, wherein an extraction phase includes a first extraction stage comprising said initially extracting and collecting a first portion of the given gas, and includes a second extraction stage comprising said subsequently extracting and collecting a second portion of the given gas, wherein the established family of calibration curves comprises sequences having the general formula:

$$q_n = q_1 \exp[-b(n-1)] \tag{1}$$

wherein n is the nth extraction stage of the extraction phase; $(q_n)$ is the quantity of given gas in the gases extracted during the nth extraction stage; $(q_1)$ is the quantity of given gas in the gases extracted during the first extraction stage; and (b) is a parameter that is independent of the content of the given gas in the calibration mud and that is dependent on characteristics of the drilling mud and on the predetermined conditions.

7. The method of claim 1, wherein said computing the content of the given gas in the drilling mud includes:
   identifying the applicable curve of the established family of calibration curves on which is located a point corresponding to the quantity of the portion of the given gas extracted from the analysis sample of the drilling mud; and
   adding the quantity of the portion of the given gas extracted from the analysis sample of the drilling mud to at least one quantity of given gas corresponding to a different point on the applicable curve.

8. The method of claim 1, wherein the drilling mud is an oil-based mud or a mud based on at least one synthetic compound.

9. The method of claim 1, wherein the calibration mud comprises at least one portion of the drilling mud.

10. A mud analyzing device for determining a content of a given gas in a drilling mud, said device comprising:
    a calibration device including:
    a first extraction member operable to:
    initially extract and collect a first portion of the given gas from a calibration sample of the drilling mud under predetermined conditions; and
    subsequently extract and collect a second portion of the given gas from the same calibration sample of the drilling mud under the predetermined conditions;

a first measuring device for measuring the first portion of the given gas extracted by said extraction member and the second portion of the given gas extracted by said first extraction member to obtain data representing a quantity of the first portion of the given gas and a quantity of the second portion of the given gas extracted from the calibration sample of drilling mud; and a curve generating section for establishing a family of calibration curves representing the given gas extracted from the drilling mud by said first extraction member, said curve generating section being operable to establish the family of calibration curves based on the data representing the quantity of the first portion of the given gas and the quantity of the second portion of the given gas; and an analysis device including:
  a second extraction member for extracting and collecting the given gas from an analysis sample of the drilling mud under the predetermined conditions;
  a second measuring device for measuring the given gas extracted from the analysis sample of the drilling mud by said second extraction member to obtain data representing a quantity of the given gas extracted from the analysis sample of the drilling mud; and
  a computing device for computing a content of the given gas in the drilling mud based on the data representing the quantity of the given gas extracted from the analysis sample of the drilling mud as measured by said second measuring device, and based on an applicable curve of the established family of calibration curves.

11. The mud analyzing device of claim 10, wherein each of said first extraction member and said second extraction member includes:
  a vessel having a stirring member;
  a conveying device for conveying the drilling mud into said vessel;
  a removal member for evacuating the drilling mud from inside said vessel to outside said vessel; and
  a sampling member for sampling from the vessel the gas extracted from the drilling mud.

12. The mud analyzing device of claim 11, wherein said first extraction member includes only a single vessel and further includes a recovery member for recovering the drilling mud at an outlet of said removal member, said recovery member being connected to an inlet of said vessel.

13. The mud analyzing device of claim 12, wherein said first extraction member consists of said second extraction member.

14. The mud analyzing device of claim 11, wherein said vessel of said first extraction member comprises a first vessel, said first extraction member further including a second vessel, said removal member being arranged to evacuate the drilling mud from said first vessel and to convey the evacuated drilling mud to said second vessel.

15. A drilling rig comprising:
  a circulation conduit for circulating drilling mud;
  said mud analyzing device of claim 10; and
  a sampling member for sampling drilling mud from said circulation conduit and conveying the sampled drilling mud to said mud analyzing device.

16. The drilling rig of claim 15, wherein each of said first extraction member and said second extraction member includes:
  a vessel having a stirring member;
  a conveying device for conveying the drilling mud into said vessel;
  a removal member for evacuating the drilling mud from inside said vessel to outside said vessel; and
  a sampling member for sampling from the vessel the gas extracted from the drilling mud.

17. The drilling rig of claim 16, wherein said first extraction member includes only a single vessel and further includes a recovery member for recovering the drilling mud at an outlet of said removal member, said recovery member being connected to an inlet of said vessel.

18. The drilling rig of claim 17, wherein said first extraction member consists of said second extraction member.

19. The drilling rig of claim 15, wherein said first extraction member includes:
  a first vessel;
  a second vessel; and
  a removal member arranged to evacuate the drilling mud from said first vessel and to convey the evacuated drilling mud to said second vessel.

* * * * *